(12) United States Patent
Muramatsu et al.

(10) Patent No.: US 10,031,152 B2
(45) Date of Patent: Jul. 24, 2018

(54) AUTOMATIC ANALYZER

(71) Applicant: HITACHI HIGH-TECHNOLOGIES CORPORATION, Tokyo (JP)

(72) Inventors: Yoshiki Muramatsu, Tokyo (JP); Takamichi Mori, Tokyo (JP); Kazuhiro Nakamura, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 76 days.

(21) Appl. No.: 15/113,309

(22) PCT Filed: Jan. 9, 2015

(86) PCT No.: PCT/JP2015/050424
§ 371 (c)(1),
(2) Date: Jul. 21, 2016

(87) PCT Pub. No.: WO2015/111442
PCT Pub. Date: Jul. 30, 2015

(65) Prior Publication Data
US 2017/0010294 A1 Jan. 12, 2017

(30) Foreign Application Priority Data
Jan. 27, 2014 (JP) ................. 2014-012070

(51) Int. Cl.
*G01N 35/10* (2006.01)
*G01N 33/49* (2006.01)

(52) U.S. Cl.
CPC ......... *G01N 35/1016* (2013.01); *G01N 33/49* (2013.01); *G01N 35/1011* (2013.01); *G01N 35/1079* (2013.01); *G01N 2035/1018* (2013.01)

(58) Field of Classification Search
None
See application file for complete search history.

(56) References Cited

U.S. PATENT DOCUMENTS 5,130,254 A 7/1992 Collier et al.
5,853,665 A 12/1998 Ade et al.
(Continued)

FOREIGN PATENT DOCUMENTS

EP 0747689 A2 12/1996
JP 11-503528 A 3/1999
(Continued)

OTHER PUBLICATIONS

Extended European Search Report received in corresponding European Application No. 15740185.2 dated Sep. 22, 2017.
(Continued)

*Primary Examiner* — P. Kathryn Wright
(74) *Attorney, Agent, or Firm* — Mattingly & Malur, PC

(57) ABSTRACT

A pressure sensor detects the inner pressure of a probe at the time of suction of a specimen and a memory stores therein a plurality of clogging detection parameters in accordance with pressure in the vacuum blood collection tube. The clogging detection parameter stored in the memory is selected in accordance with the pressure in the vacuum blood collection tube, and a determination of the clogging of the probe is performed based on the selected clogging detection parameter and the inner pressure at the time of suction of the specimen detected in the pressure sensor.

11 Claims, 7 Drawing Sheets

(56) References Cited

U.S. PATENT DOCUMENTS

| | | | |
|---|---|---|---|
| 2004/0034479 A1* | 2/2004 | Shimase | G01N 35/1016 702/19 |
| 2011/0189713 A1 | 8/2011 | Le Comte et al. | |
| 2015/0323557 A1* | 11/2015 | Tamezane | G01N 35/1009 422/67 |

FOREIGN PATENT DOCUMENTS

| | | |
|---|---|---|
| JP | 2004-125780 A | 4/2004 |
| JP | 2011-085421 A | 4/2011 |
| WO | 97/26542 A1 | 7/1997 |
| WO | 2014/013836 A1 | 1/2014 |
| WO | WO-2014013836 A1 * 1/2014 | ......... G01N 35/1009 |

OTHER PUBLICATIONS

International Search Report of PCT/JP2015/050424 dated Apr. 21, 2015.

* cited by examiner

| AMOUNT OF SUCTION | AMOUNT OF NEGATIVE PRESSURE IN VACUUM BLOOD COLLECTION TUBE | REFERENCE PARAMETER |
|---|---|---|
| 1.0μL TO 3.0μL | 0kPa TO 40kPa | I - a |
| | 41kPa TO 80kPa | I - b |
| 3.1μL TO 5.0μL | 0kPa TO 40kPa | II - a |
| | 41kPa TO 80kPa | II - b |

| EVENT No. \ CHARACTERISTIC VARIABLE No. | 1 | 2 | ... | k−1 | k |
|---|---|---|---|---|---|
| 1 | $X_{11}$ | $X_{12}$ | ... | $X_{1,k-1}$ | $X_{1k}$ |
| 2 | $X_{21}$ | $X_{22}$ | ... | $X_{2,k-1}$ | $X_{2k}$ |
| ⋮ | ... | ... | ... | ... | ... |
| n−1 | $X_{n-1,1}$ | $X_{n-1,2}$ | ... | $X_{n-1,k-1}$ | $X_{n-1,k}$ |
| n | $X_{n1}$ | $X_{n2}$ | ... | $X_{n,k-1}$ | $X_{nk}$ |

AUTOMATIC ANALYZER

TECHNICAL FIELD

The present invention relates to an automatic analyzer including a sample dispensation device and more specifically relates to an automatic analyzer performing dispensation by piercing a sealing cap of a test tube without performing uncapping processing.

BACKGROUND ART

In a biochemical automatic analyzer as an example of an automatic analyzer, for an analysis of components in a biological specimen (hereinbelow referred to as a specimen) such as blood serum and urine, the specimen and a reagent are reacted, and changes of color tone and turbidity resulting from the reaction are optically measured by a photometric unit such as a spectrophotometer.

To cause the specimen and the reagent to be reacted, dispensation thereof from containers respectively housing the specimen and the reagent to a reaction cuvette needs to be performed. For this reason, the automatic analyzer includes a dispensation device automatically sucking and discharging the specimen or the reagent from the container housing it to the reaction cuvette.

In a sample dispensation device dispensing the specimen from a test tube sealed by a sealing cap (hereinbelow referred to as a vacuum blood collection tube) to the reaction cuvette, a dispensation abnormality may occur due to various reasons. A main reason for the dispensation abnormality is probe clogging generated by suction of the specimen. When the probe is clogged, a predetermined amount of specimen cannot be dispensed into the reaction cuvette, and a reliable analysis result cannot be obtained.

As means for determining the dispensation abnormality, a large number of techniques of providing a pressure sensor inside a dispensation flow path including the probe and detecting the dispensation abnormality such as the probe clogging based on pressure fluctuation are proposed.

In a technique described in PTL 1, pressure inside a vacuum blood collection tube is monitored through a sealing cap and a piercing probe by a pressure sensor. PTL 1 describes that clogging is determined when a detection value of the pressure sensor is a threshold value or higher, or a threshold value or lower.

CITATION LIST

Patent Literature

PTL 1: JP 2011-85421 A

SUMMARY OF INVENTION

Technical Problem

However, in the above method described in PTL 1, since the amount of negative pressure inside the vacuum blood collection tube varies in accordance with a difference of the amount of the negative pressure depending on a kind of the vacuum blood collection tube and variation of the blood collection amount, general determination by a threshold value using an atmospheric pressure state as a reference may lead to erroneous determination of normal suction or abnormal suction.

In a case of using the vacuum blood collection tube, the specimen is whole blood, and the viscosity thereof is thus around 40% when compared to a glycerol aqueous solution. Also, the pressure of the vacuum blood collection tube including a test tube and the sealing cap is set to be negative in advance, and the amount of the negative pressure varies individually depending on the kind of the blood collection tube and how much blood can be sucked into the blood collection tube. Further, at the time of sucking the specimen, segmenting air separating water from the specimen is provided in the probe. The probe is depressurized by the amount of the negative pressure when the probe is inserted into the vacuum blood collection tube, and the segmenting air moves to the specimen side.

Since the specimen is sucked in a state in which the segmenting air has moved to the specimen side, the amount of the segmenting air in the probe varies depending on the degree of the negative pressure in the vacuum blood collection tube. When the amount of the segmenting air differs, the pressure at the time of suction differs even in a case in which the same specimen is sucked. As a result, the variation of the amount of the negative pressure in the vacuum blood collection tube causes the variation of the amount of the segmenting air, which leads to a high risk of regarding normal suction as abnormal suction.

The present invention is accomplished by taking such problems as mentioned above into consideration thereof, and an object thereof is to avoid an influence generated by variation of the amount of negative pressure in a vacuum blood collection tube due to a kind of and the amount of collected blood in the vacuum blood collection tube and detect abnormal dispensation caused by clogging more accurately.

Solution to Problem

To solve the above problems, a configuration described in the patent claims is employed, for example.

The present invention includes a plurality of means for solving the above problems, and an example thereof is raised as follows.

An automatic analyzer includes: a probe passing through a cap of a cappeded vacuum blood collection tube, sucking a specimen inside the vacuum blood collection tube, and discharging the specimen into a reaction cuvette; a syringe causing the probe to suck and discharge the specimen; a dispensation flow path connecting the syringe; a pressure sensor arranged in the dispensation flow path and detecting inner pressure of the probe at time of suction of the specimen; a memory having stored therein a plurality of clogging detection parameters in accordance with pressure in the vacuum blood collection tube for a same suction amount of the specimen; and a controller selecting the clogging detection parameter stored in the memory in accordance with the pressure in the vacuum blood collection tube and performing clogging determination of the probe based on the selected clogging detection parameter and the inner pressure at the time of suction of the specimen detected in the pressure sensor.

Advantageous Effects of Invention

By measuring the amount of pressure in the vacuum blood collection tube in advance before suction of the specimen, how the amount of segmenting air in the probe changes with respect to a design value can be estimated. According to the present invention, since the plurality of clogging detection parameters are stored in the analyzer in accordance with the amount of the pressure in the blood collection tube as threshold values for use in clogging detection, and an optimal clogging detection parameter can be selected in accordance with the amount of negative pressure in the vacuum blood collection tube, the reliable automatic analyzer can be provided.

DESCRIPTION OF EMBODIMENTS

Hereinbelow, embodiments of the present invention will be described with reference to the drawings.

Figure 1:
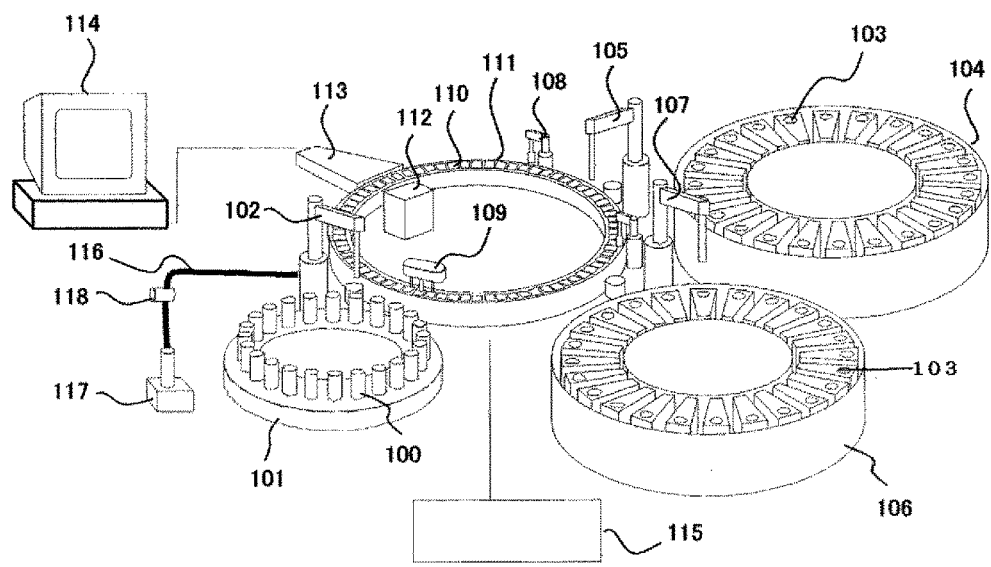
FIG. 1 is a schematic configuration diagram of an automatic analyzer to which the present invention is applied.

FIG. 1 is a schematic configuration diagram of an automatic analyzer to which the present invention is applied.

In FIG. 1, the automatic analyzer includes a sample disk (specimen disk) 101 enabling a plurality of sample containers (specimen containers) 100 holding a specimen to be mounted thereon, a first reagent disk 104 and a second reagent disk 106 enabling a plurality of reagent containers 103 holding a reagent to be mounted thereon, and a reaction disk 111 arranging a plurality of reaction cuvettes 110 therearound.

The automatic analyzer also includes a probe (specimen probe) 102 dispensing the specimen sucked from the sample container 100 into the reaction cuvette 110, a first reagent probe 105 dispensing the reagent sucked from the reagent container 103 in the first reagent disk 104 into the reaction cuvette 110, and a second reagent probe 107 dispensing the reagent sucked from the reagent container 103 in the second reagent disk 106 into the reaction cuvette 110.

The automatic analyzer further includes a stirring device 108 stirring a liquid in the reaction cuvette 110, a cuvette cleaning mechanism 109 cleaning the reaction cuvette 110, a light source 112 provided around an inner circumference of the reaction disk 111, a spectrophotometric detector 113, a computer 114 connected to the spectrophotometric detector 113, and a controller 115 controlling operations of the entire automatic analyzer and exchanging data with an external unit.

The probe 102 is connected via dispensation flow paths 116 and 119 to a metering pump 117, and a pressure sensor 118 is provided in the middle of the dispensation flow paths 116 and 119. The pressure sensor 118 arranged in the dispensation path can detect inner pressure of the probe at the time of suction of the specimen.

Figure 2:
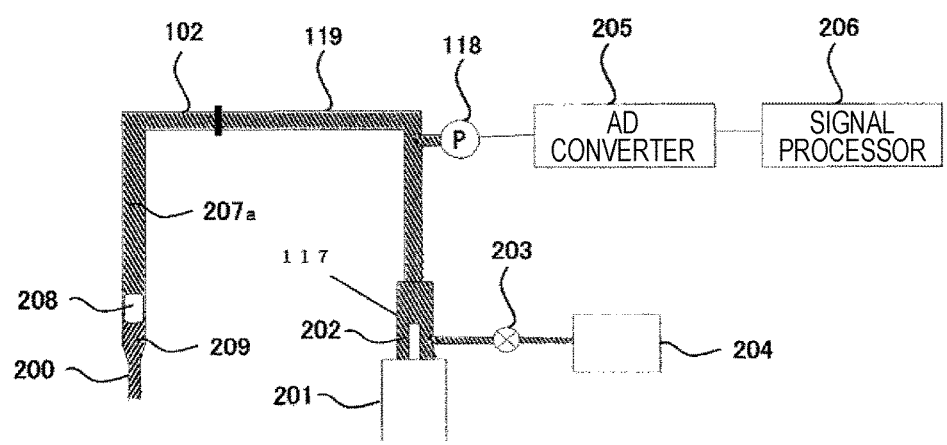
FIG. 2 describes a main part (a pressure signal processing unit) according to an embodiment of the present invention.

FIG. 2 describes a main part (a pressure signal processing unit in the probe 102) according to an embodiment of the present invention.

In FIG. 2, the probe 102 is provided at a tip end thereof with a reduced portion 200 having a smaller cross-sectional area than those of other parts. Also, the metering pump 117 is provided with a plunger 202 (also referred to as a syringe) driven by a driving mechanism 201. The metering pump 117 is connected via a valve 203 to a pump 204. To the syringe is connected the pipe 119 (dispensation flow path), and by driving of the syringe, the specimen can be sucked into the probe 102 or discharged out of the probe 102.

Also, the pressure sensor 118 is connected via an AD converter 205 to a signal processor (signal processing unit) 206. The inside of the probe 102 is filled with a system liquid 207, and a specimen 209 is sucked via segmenting air 208 into the probe 102. An example in FIG. 2 illustrates a state in which the specimen 209 has been sucked into the sample probe 102.

The probe 102 includes a not-illustrated moving mechanism and can move vertically and be rotated between the sample container 100 and the reaction cuvette 110.

Next, operations according to the embodiment of the present invention will be described.

In FIGS. 1 and 2, the sample container 100 is filled with a specimen under test such as blood serum and is set in the sample disk 101. A kind of an analysis required for each specimen is input into the controller 115 via the computer 114. A specific amount of the specimen collected from the sample container 100 by the sample probe 102 is dispensed into the reaction cuvette 110 arranged in the reaction disk 111. The sample probe is a probe passing through a cap of a capped vacuum blood collection tube, sucking the specimen inside the blood collection tube, and discharging the specimen into the reaction cuvette 110.

Subsequently, a specific amount of a reagent is dispensed from the reagent container 103 installed in the first reagent disk 104 or the second reagent disk 106 into the reaction cuvette 110 by the first reagent probe 105 or the second reagent probe 107, and the specimen and the reagent are stirred by the stirring device 108. The dispensation amounts of the specimen and the reagent are preset per kind of the analysis.

The reaction disk 111 periodically repeats rotation and stop, and photometric measurement is performed by the spectrophotometric detector 113 at a time when the reaction cuvette 110 passes in front of the light source 112. During a 10-minute reaction period, the photometric measurement is repeated by the spectrophotometric detector 113, and drainage of the reaction liquid inside the reaction cuvette 110 and cleaning of the reaction cuvette 110 are thereafter performed by the cuvette cleaning mechanism 109. During the operation, an operation in another reaction cuvette 110 with use of another specimen and another reagent is performed in parallel. Data obtained by the photometric measurement of the spectrophotometric detector 113 is calculated by the computer 114, and the computer 114 calculates a concentration of a component in accordance with the kind of the analysis and displays the concentration on a display thereof.

Operations of the probe 102 will be described in detail.

Before suction of the specimen, the controller 115 first opens or closes the valve 203 to fill the inside of the flow path of the sample probe 102 with the system liquid 207 supplied from the pump 204. The controller 115 then causes the plunger 202 to be lowered by the driving mechanism 201 in a state in which the tip end of the probe 102 is in the air to suck the segmenting air 208.

Subsequently, the controller 115 lowers the probe 102 into the sample container 100 and lowers the plunger 202 as much as a predetermined amount in a state in which the tip end soaks in the specimen to suck the specimen into the probe 102. In this case, the sucked liquid 209 is the specimen. Pressure fluctuation in the probe 102 during the operation continued from suction is detected by the pressure sensor 118, is converted into digital data by the AD converter 205, and is transmitted to the signal processor 206. The probe 102 thereafter moves to a place above the reaction cuvette 110 and discharges the specimen.

Pressure fluctuation in the probe 102 during the operation continued from discharge of the specimen is detected by the pressure sensor 118 again, is converted into digital data by the AD converter 205, and is transmitted to the signal processor 206. Subsequently, the inside and the outside of the probe 102 are cleaned by opening and closing the valve 203 to be prepared for a subsequent analysis.

The signal processor 206 determines whether or not there is a dispensation abnormality from the pressure waveforms at the time of suction and discharge of the specimen of the probe 102. In a case in which it is determined that there is an abnormality, the signal processor 206 stops the analysis, displays an alarm on the display unit of the computer 114 or the like, and performs a recovery operation. As the recovery operation, one out of eliminating a cause for the abnormality and re-dispensing, moving to a test of another specimen, stopping the analyzer, and the like is selected.

Figure 3:
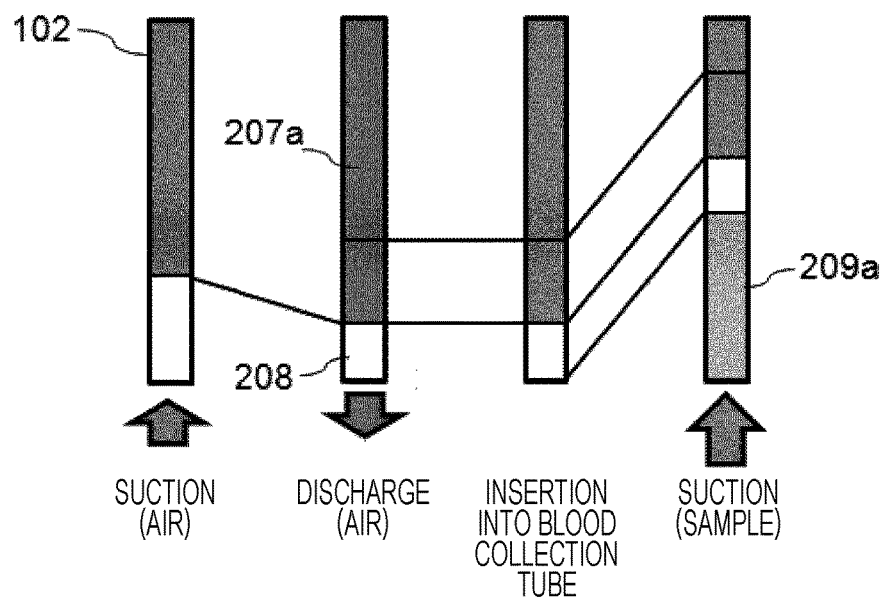
FIG. 3 illustrates state changes in a probe from time directly before a start of suction of a specimen to time directly after an end in an atmospheric pressure state.

FIG. 3 illustrates states in the probe in a case in which the operation up to the suction of the specimen has been performed in an atmospheric pressure state.

A specific amount of the segmenting air 208 is sucked into the probe 102 filled with system water 207a, and a specific amount of the segmenting air 208 is discharged, to set a specific amount of the segmenting air 208. For example, 10 µL is sucked, and 6 µL is discharged, to set 4 µL of the segmenting air. This operation is an operation to cancel an individual difference of the backrush (hereinbelow, BL) amount of the syringe.

Figure 4:
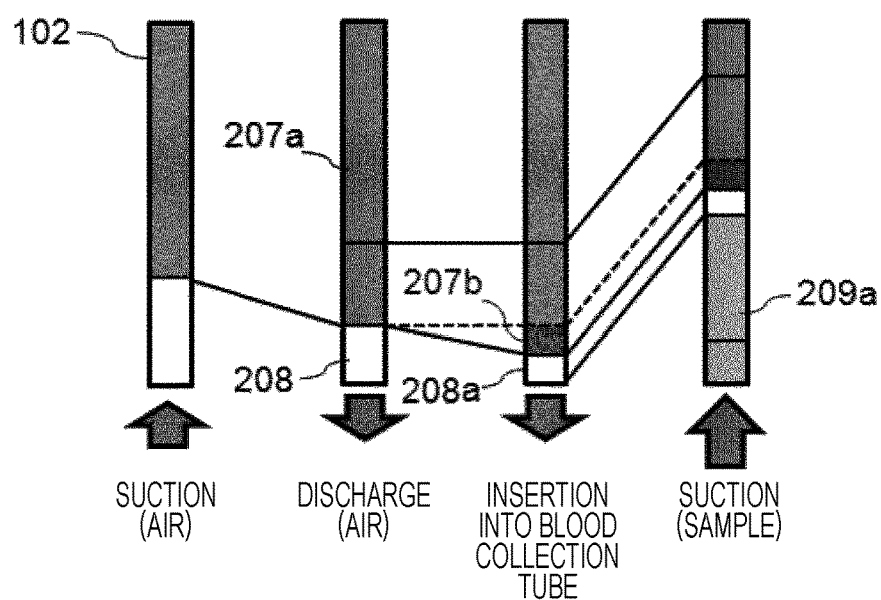
FIG. 4 illustrates state changes in the probe from time directly before the start of suction of the specimen to time directly after the end in a negative pressure state.

FIG. 4 illustrates states in the probe in a case in which the operation up to the suction of the specimen has been performed when the blood collection tube is in a negative pressure state.

When the probe 102 is inserted into the vacuum blood collection tube in a negative pressure state, the pipe 119 from the syringe to the probe is deformed due to the negative pressure in the blood collection tube in comparison to the case in the atmospheric pressure state, the amount of the segmenting air 208 decreases as much as system water 207b, and segmenting air 208a is set.

Figure 5:
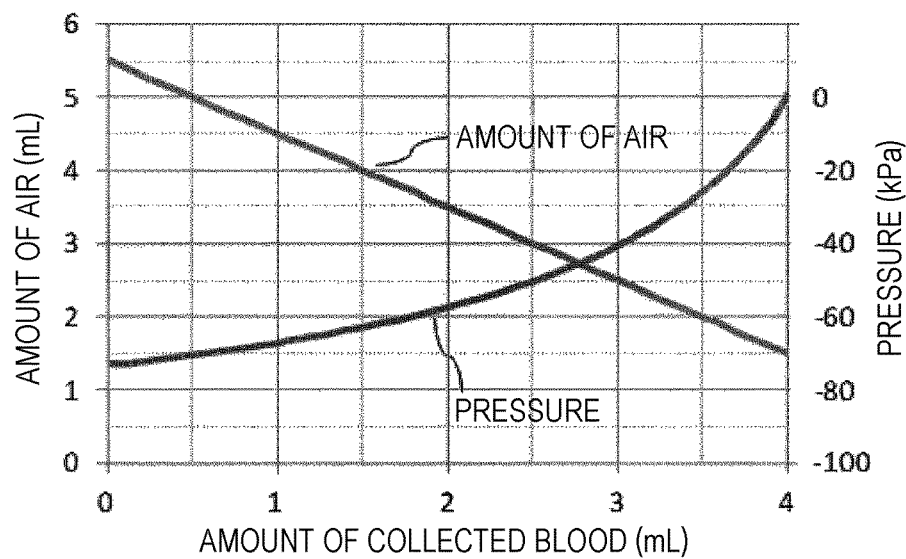
FIG. 5 illustrates pressure changes in a vacuum blood collection tube having an equal size in accordance with the amount of collected blood.

FIG. 5 illustrates pressure changes in the vacuum blood collection tube having equal specifications in accordance with the amount of collected blood.

In FIG. 5, the vertical axis represents the amount of air and pressure in the vacuum blood collection tube while the horizontal axis represents the amount of collected blood in the vacuum blood collection tube. The straight line illustrated in FIG. 5 represents relationship between the amount of air and the amount of collected blood, and the curved line represents relationship between the amount of collected blood and the pressure. It is apparent that the pressure in the vacuum blood collection tube differs depending on the amount of collected blood.

As illustrated in FIG. 5, it is apparent that the amount of negative pressure in the vacuum blood collection tube is larger as the amount of collected blood is smaller, and that the pressure is closer to the atmospheric pressure as the amount of collected blood is larger. Since the amount of collected blood that can be collected from a patient is not necessarily constant, the data of pressure in the vacuum blood collection tube varies even with use of the vacuum blood collection tube of the same size.

Figure 6:
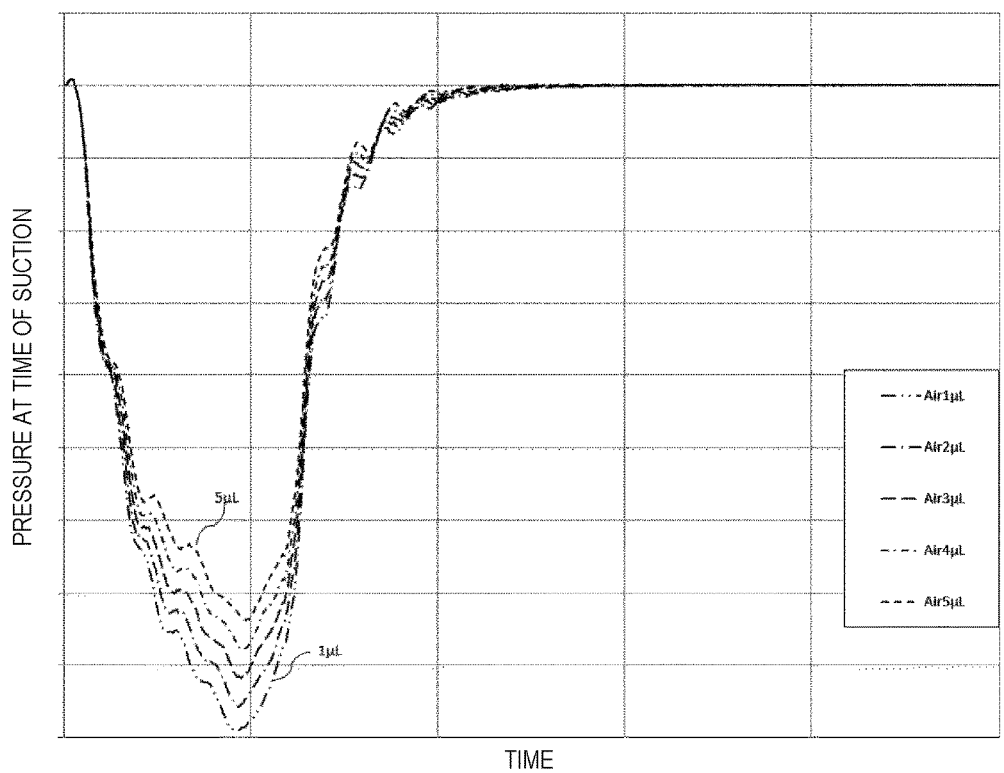
FIG. 6 illustrates brief forms of outputs of a pressure sensor at the time of suction of the specimen.

FIG. 6 illustrates brief forms of outputs of the pressure sensor 118 from the time when suction of the specimen is started.

In FIG. 6, the vertical axis represents pressure based on an output of the pressure sensor 118 while the horizontal axis represents time. Also, the difference in the amount of segmenting air is expressed by line kinds. The waveforms illustrated in FIG. 6 illustrate pressure fluctuation at the time of suction of the specimen depending on the amount of segmenting air, and it is apparent that the pressure waveform at the time of suction changes even with use of the same specimen depending on the amount of segmenting air.

As illustrated in FIG. 6, the pressure at the time of suction is lower as the amount of segmenting air is smaller. In a case in which the specimen is to be actually sucked in a state in which the pressure inside the vacuum blood collection tube is negative pressure, the amount of segmenting air changes depending on the amount of negative pressure as illustrated in FIG. 4. The actual amount of negative pressure in the vacuum blood collection tube individually varies, and the actual amount of segmenting air in the probe before suction of the specimen varies depending on the amount of negative pressure in the vacuum blood collection tube.

Also, the specimen to be sucked from the vacuum blood collection tube is whole blood, and the viscosity thereof is around 40% when compared to a glycerol aqueous solution. The pressure waveform at the time of suction changes even with use of the same specimen depending on the amount of segmenting air, which leads to a high risk of regarding normal suction as abnormal suction.

Figures 7, 8:
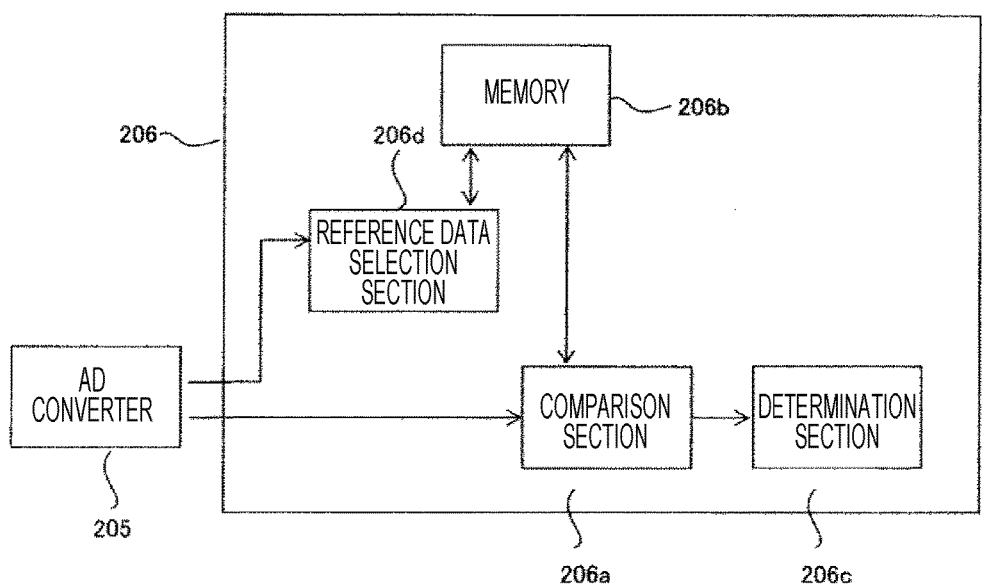
FIG. 7 is an internal configuration diagram of a signal processor according to the present embodiment.
FIG. 8 illustrates an example of selection of a reference parameter in a reference parameter selection section.

FIG. 7 is an internal configuration diagram of the signal processor 206 according to the present embodiment.

In FIG. 7, the signal processor 206 includes a reference parameter selection section 206d, a memory 206b, a comparison section 206a, and a determination section 206c. The determination section 206c of the signal processor 206 transmits a determination result thereof to the controller 115. The signal processor 206 may be provided separately from the controller 115 or inside the controller 115. It is to be noted that the reference parameter is referred to as a clogging detection parameter in some cases.

As described below, the memory 206b is a memory having stored therein a plurality of clogging detection parameters in accordance with pressure in the vacuum blood collection tube for the same suction amount of the specimen.

FIG. 8 illustrates an example of selection of the reference parameter in the reference parameter selection section 206d. Here, as one embodiment, the amount of suction is set to 1.0 µL to 3.0 µL and 3.1 µL to 5.0 µL, and the amount of negative pressure in the vacuum blood collection tube is set to 0 kPa to 40 kPa and 41 kPa to 80 kPa.

In FIG. 8, the reference parameter selection section 206d selects a reference parameter from the plurality of reference parameters in accordance with the amount of negative pressure in the vacuum blood collection tube depending on the range of the suction amount and uses it as the clogging detection parameter at the time of suction of the specimen. That is, the controller 115 selects a clogging detection parameter stored in the memory 206b in accordance with the pressure in the vacuum blood collection tube and performs clogging determination of the probe 102 based on the selected clogging detection parameter and the inner pressure at the time of suction of the specimen detected in the pressure sensor.

In the present description, a case in which two reference parameters are set as reference parameters to be selected depending on the state of the negative pressure in the blood collection tube is illustrated. However, since the amount of negative pressure in the blood collection tube significantly differs depending on the amount of collected blood, the reference parameters may be set more finely, and two or more reference parameters may be set.

Measurement of the amount of negative pressure needs to be completed before the probe is dipped into the specimen or before the probe sucks the specimen after the probe is inserted into the vacuum blood collection tube. The reason for this is that selection of the reference parameter needs to be completed at the time of suction of the specimen.

Next, the reference parameter will be described. For example, the reference parameter is a parameter to be used to calculate a statistical distance between the parameter and pressure. In the clogging determination, the controller 115 obtains a pressure waveform at the time of suction of the specimen (that is, a detection result of the pressure sensor 118) and a reference parameter selected by the reference parameter selection section 206d from among the plurality of reference parameters stored in the memory 206b and calculates a statistical distance between these. In the present embodiment, a case in which Mahalanobis' distance is used as the statistical distance used in the comparison section 206a will be illustrated in the description.

The controller 115 compares the calculated statistical distance with a threshold value in the comparison section 206a and performs clogging determination of the probe based on the comparison result in the determination section 206c. The threshold value stored in the memory 206b is defined per target for dispensation processing or per dispensation amount in advance. It is to be noted that the same threshold value may be used for the same dispensation amount. This can simplify the comparison processing in the comparison section 206a.

Next, the statistical distance will be described. The statistical distance is an index derived by quantifying a similarity between two events represented by a plurality of characteristic variables. In a case of the present embodiment, how far target data is from a set of known data prepared in advance is calculated. Here, a method for calculating the Mahalanobis' distance as an example of the statistical distance will be described.

Figures 9, 10A:
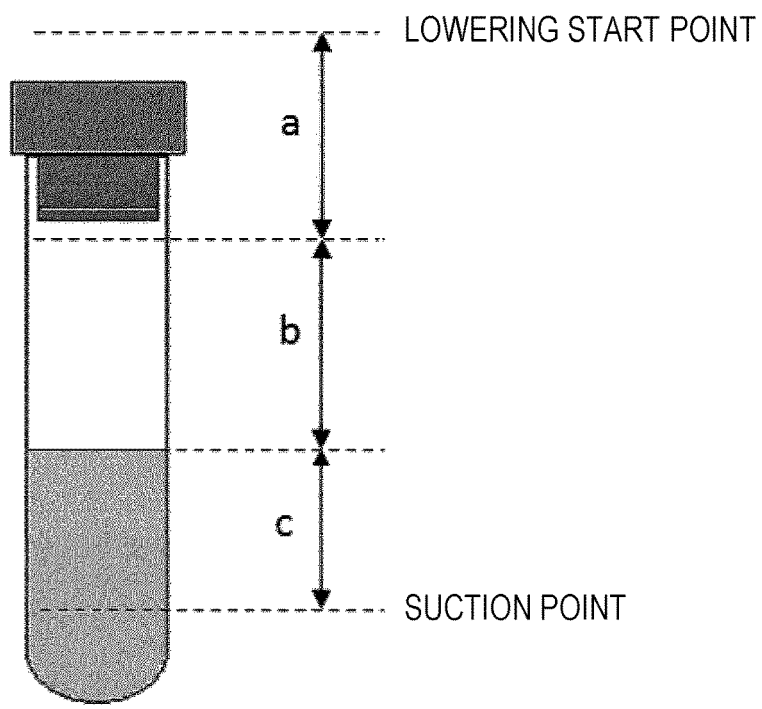
FIG. 9 schematically illustrates an example of a set of known data.
FIG. 10A is a schematic view illustrating a range of the vacuum blood collection tube.

FIG. 9 schematically illustrates an example of a set of reference parameters. In this set of the reference parameters, each of data of n events has k characteristic variables (where n and k are positive integers).

In calculation of the Mahalanobis' distance, normalization is first performed by (Equation 1) shown below in a case in which respective characteristic variables of target data are $y_1, y_2, \ldots, y_k$, averages of respective characteristic variables of known data $x_{nk}$ are $z_1, z_2, \ldots, z_k$, and standard deviations are $\sigma_1, \sigma_2, \ldots, \sigma_k$. Note that $i=1, \ldots, k$.

$$X_i = \frac{y_i - z_i}{\sigma_i} \quad \text{(Equation 1)}$$

Subsequently, a Mahalanobis' distance $D_M$ of the target data from the set of the reference parameters is expressed by (Equation 2) shown below.

$$D_M = \sqrt{\frac{1}{k}(X_1 \ \ldots \ X_k) A \begin{pmatrix} X_1 \\ \vdots \\ X_k \end{pmatrix}} \quad \text{(Equation 2)}$$

In this manner, the Mahalanobis' distance $D_M$, which is a statistical distance, can be calculated, and by comparing the Mahalanobis' distance with a predetermined threshold value, the clogging determination of the probe can be performed.

For example, the known data $x_{nk}$ corresponds to a pressure value of an ideal pressure waveform at a predetermined time, and this is a reference parameter. The respective characteristic variables of the target data are derived from a pressure waveform at the time of suction of a specimen targeted for the clogging detection, and with use of the averages and standard deviations of the respective characteristic variables of the known data $x_{nk}$, the Mahalanobis' distance $D_M$ can be calculated by Equation 1 and Equation 2.

In the present embodiment, this known data $x_{nk}$ is expressed as I-a in FIG. 8, and the plurality of reference parameters are stored in the memory in accordance with the amount of the negative pressure in the vacuum blood collection tube. I-b is different known data $x'_{nk}$ from I-a. The controller selects a reference parameter in accordance with pressure in the vacuum blood collection tube for the same suction amount, calculates a statistical distance, and compares the calculated statistical distance with the threshold value, to enable the clogging determination of the probe. Meanwhile, as illustrated in FIG. 8, for the different amount of suction, it is preferable to store a plurality of reference parameters II-a and II-b in the memory in accordance with the amount of negative pressure in a similar manner.

Meanwhile, instead of the Mahalanobis' distance, other examples of the method for calculating the statistical distance that can be applied to the present embodiment are calculation methods such as Euclidean distance, standardized Euclidean distance, Manhattan distance, Chebyshev distance, Minkowski distance, and multivariate normal density.

Meanwhile, the reference parameter also includes a minimum pressure value of the ideal pressure waveform at a predetermined amount of negative pressure in the vacuum blood collection tube, and in a case in which a pressure waveform at the time of suction of the specimen falls below this minimum value, clogging may be determined. In this case, respective unique minimum values in accordance with the amount of negative pressure are stored in the memory, and the controller selects a minimum value serving as a threshold value for the clogging determination in accordance with the measured amount of negative pressure. Meanwhile, as a threshold value for the clogging determination, a pressure value at a predetermined time may be used.

Figure 10B:
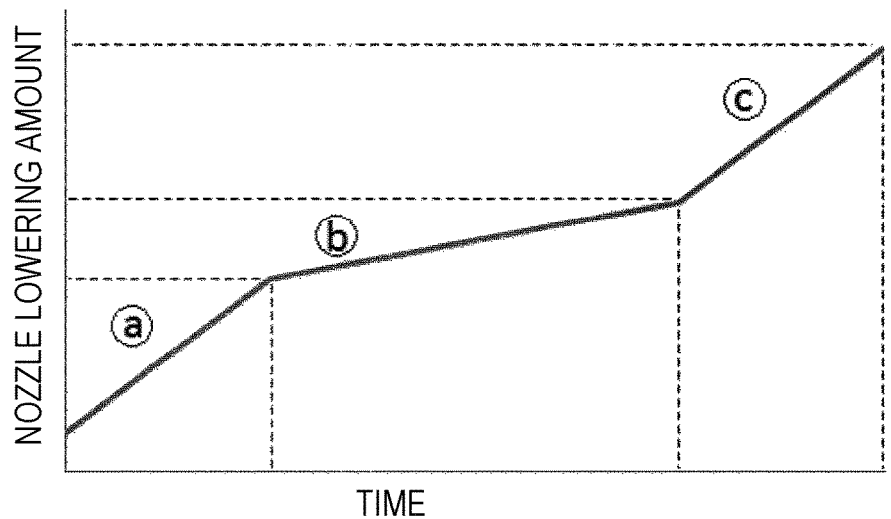
FIG. 10B illustrates relationship between lowering time and a lowering amount of a nozzle in the vacuum blood collection tube.
Figure 10C:
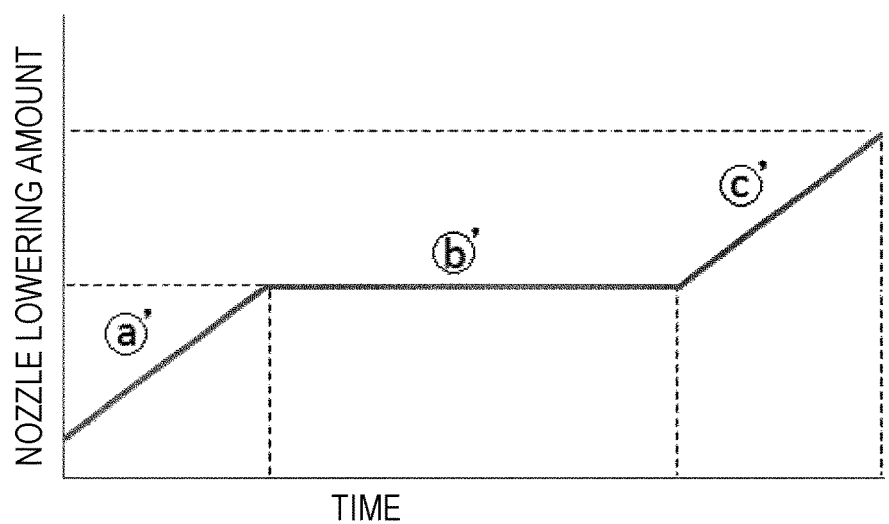
FIG. 10C illustrates relationship between the lowering time and the lowering amount of the nozzle in the vacuum blood collection tube.

FIG. 10A is a schematic view illustrating a range of the vacuum blood collection tube. In FIG. 10A, a represents a range from an outside of the vacuum blood collection tube to an inside of the vacuum blood collection tube, b represents a range from the inside of the vacuum blood collection tube to a liquid level of the specimen, and c represents a range from the liquid level of the specimen to a suction position. FIGS. 10B and 10C illustrate relationship between lowering time and a lowering amount of the nozzle in the vacuum blood collection tube.

Examples of an operation when the probe is inserted into the vacuum blood collection tube are a method of lowering the probe quickly in the range (a), decreasing the lowering speed in the range (b), in which negative pressure in the vacuum blood collection tube is measured, and lowering the probe to the suction position at high speed in the range (c) after measurement of the vacuum pressure as in FIG. 10B and a method of lowering the probe quickly in the range (a)', pausing in the range (b)', in which negative pressure in the vacuum blood collection tube is measured, and lowering the probe to the suction position at high speed in the range (c)' after measurement of the vacuum pressure as in FIG. 10C. Such control of lowering the probe is performed by the controller 115.

That is, it is preferable for the controller 115 to control the lowering operation of the nozzle. It is preferable for the controller to decrease the speed of the lowering operation further than the lowering speed when the nozzle passes through the cap of the vacuum blood collection tube or stop the lowering operation to measure pressure in the vacuum blood collection tube. The reason for this is not to take too long time until suction of the specimen and to improve sensitivity of pressure measurement.

It is also preferable for the controller 115 to decrease the speed of the lowering operation further than the lowering speed when the nozzle passes through the cap of the vacuum blood collection tube to measure pressure in the vacuum blood collection tube and perform the lowering operation during movement from the liquid level of the specimen to the suction position at higher speed than the decreased speed. The reason for this is to perform suction of the specimen without taking too long time.

Also, in the measurement of the amount of negative pressure in the blood collection tube, the amount of negative pressure may be measured by a suction operation of the syringe in the air layer in the vacuum blood collection tube to improve measurement sensitivity.

Figure 11:
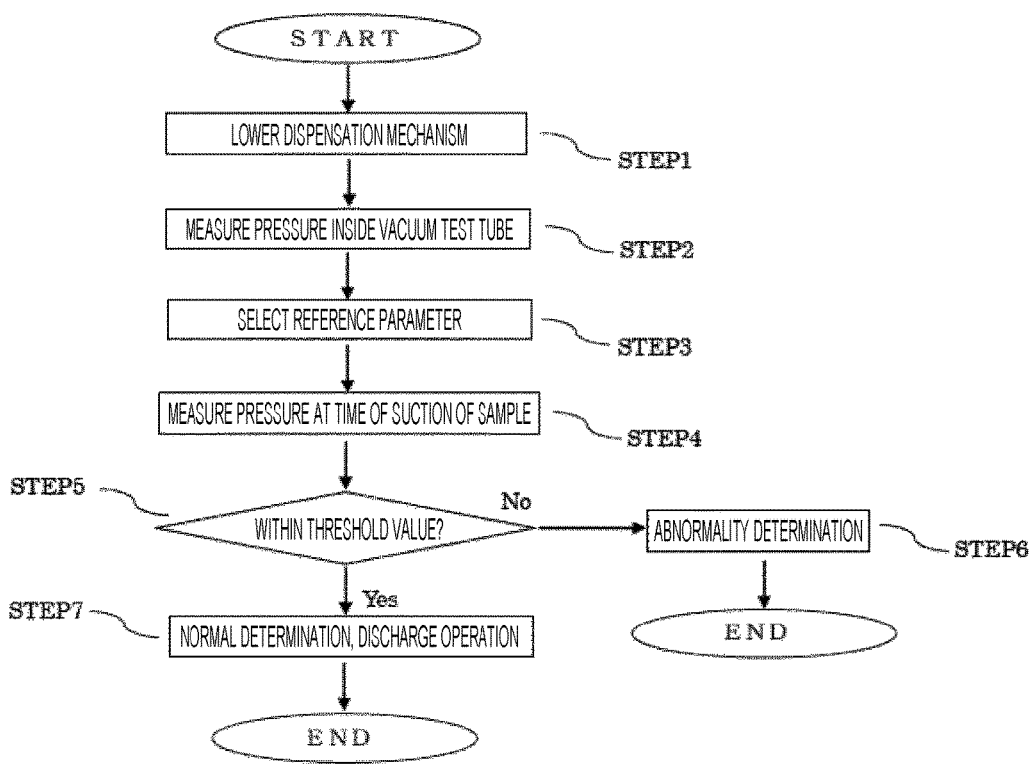
FIG. 11 is a flowchart of a determination operation according to the present invention.

FIG. 11 is a flowchart of a determination operation according to the present invention.

In FIG. 11, a lowering operation of the probe 102 is performed (STEP 1), and after insertion of the vacuum blood collection tube, pressure in the vacuum blood collection tube is measured in the pressure sensor 118 (STEP 2). The pressure measurement in the vacuum blood collection tube in this step has only to be detection of pressure in the vacuum blood collection tube, and a state of the lowering operation does not manner as in the above description.

Subsequently, the reference parameter selection section 206d selects a reference parameter based on a pressure waveform digital signal transmitted from the AD converter 205 (STEP 3) and holds the reference parameter in the memory 206b. As for the selection of the reference parameter in this step, the measurement (STEP 2) and the selection of the reference parameter (STEP 3) need to be performed during the period from passing through the sealing cap of the vacuum blood collection tube to contact with the liquid level of the specimen.

Subsequently, a suction operation of the specimen is performed in the probe 102, and pressure data at the time of suction of the specimen is measured in the pressure sensor 118 (STEP 4).

Comparison of the pressure data at the time of suction of the specimen with a predetermined threshold value stored in the memory 206b is performed in the comparison section 206a (STEP 5), and the result is supplied to the determination section 206c.

In a case in which the pressure data at the time of suction of the specimen is out of the threshold value, the determination section 206c determines that the suction is abnormal (STEP 6).

In a case in which the pressure data at the time of suction of the specimen is within the threshold value in STEP 5, the processing moves onto a discharge operation according to an instruction from the determination section 206c by means of control of the controller 115 (STEP 7).

As described above, according to the present invention, it is possible to provide an automatic analyzer avoiding an influence of characteristics such as a blood collection tube and the amount of collected blood, accurately determining an abnormality at the time of dispensation, and having high reliability.

Meanwhile, although the clogging detection parameter is selected with use of the pressure result of the pressure sensor 118 in the present embodiment, the pressure result of this pressure sensor does not need to be used as long as the clogging detection parameter can be selected in accordance with pressure in the vacuum blood collection tube. However, by using the pressure result of the pressure sensor 118, an appropriate pressure result for selecting the clogging detection parameter can be obtained without using another pressure detection mechanism.

Also, it is preferable for the controller 115 to measure pressure in the vacuum blood collection tube by means of the pressure sensor 118 after passing of the probe through the cap and before suction of the specimen. Since pressure in the vacuum blood collection tube directly before suction of the specimen can be measured, more accurate pressure can be derived than in a method of measuring or estimating pressure in the vacuum blood collection tube by means of another pressure detection mechanism before passing through the cap.

Also, although a case in which pressure in the vacuum blood collection tube is negative pressure has been described in the present embodiment, the clogging determination is valid even in a case in which pressure in the vacuum blood collection tube is positive pressure, and it is to be understood that the present technique is not limited to the case of the negative pressure.

REFERENCE SIGNS LIST 100 sample container
101 sample disk
102 sample probe
103 reagent container
104 first reagent disk
105 first reagent probe
106 second reagent disk
107 second reagent probe
108 stirring device
109 cuvette cleaning mechanism 110 reaction cuvette
111 reaction disk
112 light source
113 spectrophotometric detector
114 computer
115 controller
116 dispensation flow path
117 metering pump
118 pressure sensor
119 pipe
200 reduced portion
201 driving mechanism
202 plunger
203 valve
204 pump
205 A/D converter
206 signal processor
206a comparison section
206b memory
206c determination section
206d reference parameter selection section
207a system water
207b system water
208 segmenting air
208b segmenting air
209 specimen

The invention claimed is:

1. An automatic analyzer comprising:
a vacuum blood collection tube having a cap and containing a specimen at a negative pressure therein;
a reaction cuvette;
a probe configured to pass through the cap of the vacuum blood collection tube, suck the specimen inside the vacuum blood collection tube, and discharge the specimen into the reaction cuvette;
a photometer configured to detect light that is transmitted through the reaction container containing a solution including the specimen;
a syringe causing the probe to suck and discharge the specimen;
a dispensation flow path connecting the syringe and the probe;
a pressure sensor arranged in the dispensation flow path and detecting an inner pressure of the probe;
a memory having stored therein a plurality of clogging detection parameters in accordance with a plurality of predetermined negative pressures for a same suction amount of the specimen; and
a controller configured to select one of the clogging detection parameters stored in the memory in accordance with the negative pressure in the vacuum blood collection tube, calculate a statistical distance between the selected clogging detection parameter and the inner pressure of the probe detected by the pressure sensor at the time of suctioning the specimen, and perform a clogging determination of the probe based on comparing the calculated statistical distance with a threshold value.

2. The automatic analyzer according to claim 1, wherein the probe is determined to be clogged when the calculated statistical distance is outside the threshold value, and
wherein the probe is determined to not be clogged when the calculated statistical distance is within the threshold value.

3. The automatic analyzer according to claim 1, wherein the controller is further configured to detect the negative pressure in the vacuum blood collection tube with the pressure sensor.

4. The automatic analyzer according to claim 2, wherein the negative pressure in the vacuum blood collection tube is measured after passing of the probe through the cap and before suctioning the specimen.

5. The automatic analyzer according to claim 3, wherein the negative pressure in the vacuum blood collection tube is measured after passing of the probe through the cap and before suctioning the specimen.

6. The automatic analyzer according to claim 4, wherein the controller is further configured to measure the negative pressure in the vacuum blood collection tube by means of a suction operation of the syringe.

7. The automatic analyzer according to claim 5, wherein the controller is further configured to measure the negative pressure in the vacuum blood collection tube by means of a suction operation of the syringe.

8. The automatic analyzer according to claim 4, wherein the controller is further configured to control a lowering operation of the probe, and
wherein the probe is lowered at a first speed that is decreased or stopped when the probe passes through the cap to measure the negative pressure in the vacuum blood collection tube.

9. The automatic analyzer according to claim 5, wherein the controller is further configured to control a lowering operation of the probe, and
wherein the probe is lowered at a first speed that is decreased or stopped when the probe passes through the cap to measure the negative pressure in the vacuum blood collection tube.

10. The automatic analyzer according to claim 8, wherein the probe is lowered to a suction position at a second speed higher than the first speed after the negative pressure in the vacuum blood collection tube is measured.

11. The automatic analyzer according to claim 9, wherein the probe is lowered to a suction position at a second speed higher than the first speed after the negative pressure in the vacuum blood collection tube is measured.

* * * * *